United States Patent
Khare et al.

(10) Patent No.: US 11,382,510 B2
(45) Date of Patent: Jul. 12, 2022

(54) BIOLOGICAL DATA TRACKING SYSTEM AND METHOD

(71) Applicant: SPORTS DATA LABS, INC., Royal Oak, MI (US)

(72) Inventors: Vivek Khare, Cupertino, CA (US); Stan Mimoto, Bethel Island, CA (US); Mark Gorski, Royal Oak, MI (US)

(73) Assignee: SPORTS DATA LABS, INC., Royal Oak, MI (US)

( * ) Notice: Subject to any disclaimer, the term of this patent is extended or adjusted under 35 U.S.C. 154(b) by 0 days.

(21) Appl. No.: 16/274,701

(22) Filed: Feb. 13, 2019

(65) Prior Publication Data

US 2020/0253476 A1    Aug. 13, 2020

(51) Int. Cl.
| | |
|---|---|
| *G06F 3/048* | (2013.01) |
| *A61B 5/00* | (2006.01) |
| *G06F 3/0483* | (2013.01) |
| *G06F 3/0482* | (2013.01) |

(52) U.S. Cl.
CPC .......... *A61B 5/0022* (2013.01); *A61B 5/7475* (2013.01); *G06F 3/0482* (2013.01); *G06F 3/0483* (2013.01)

(58) Field of Classification Search
CPC ... A61B 5/0022; A61B 5/7475; G06F 3/0482; G06F 3/0483
See application file for complete search history.

(56) References Cited

U.S. PATENT DOCUMENTS

| | | | |
|---|---|---|---|
| 2008/0208016 A1* | 8/2008 | Hughes | A61B 5/0533 600/301 |
| 2013/0080185 A1* | 3/2013 | Picard | A61B 5/0531 705/2 |
| 2014/0081089 A1* | 3/2014 | O'Neill | A61B 5/7475 600/301 |
| 2014/0223421 A1* | 8/2014 | Carter | A61B 5/0024 717/168 |
| 2015/0082167 A1 | 3/2015 | Yeh et al. | |
| 2016/0240100 A1 | 8/2016 | Rauhala et al. | |
| 2017/0212210 A1* | 7/2017 | Chen | G01S 5/06 |
| 2017/0266496 A1 | 9/2017 | Case, Jr. et al. | |
| 2017/0272842 A1* | 9/2017 | Touma | A63B 43/00 |

OTHER PUBLICATIONS

Notification of International Search Report and Written Opinion dated Apr. 27, 2020 for PCT/US20/018063 filed Feb. 13, 2020, 10 pgs.

(Continued)

*Primary Examiner* — Ankit D Tejani
*Assistant Examiner* — Joshua Brendon Solomon
(74) *Attorney, Agent, or Firm* — Brooks Kushman P.C.

(57) ABSTRACT

A browser-based biological tracking system connects a computer to a set of wearable sensors. The system includes an application that is automatically downloaded from a server in response to a user accessing a webpage. The application sends data streams from the sensors to the server. The server calculates readings which are then displayed in a webpage. The set of sensors may include multiple types of sensors which utilize different communication interfaces. Some readings, called aggregate insights, are computed based on measurements from multiple sensors.

25 Claims, 9 Drawing Sheets

(56) References Cited

OTHER PUBLICATIONS

Website https://webbluetoothcg.github.io/web-bluetooth/ "Web Bluetooth—Draft Community Group Report" Dated Jan. 9, 2019, Retrieved from the Internet on Jan. 10, 2019, 101 pgs.
Website: https://aircable.com/shop/product/acc1615-aircable-host-xr5-85 "AIRcable Host XR5", Copyright Wireless Cables Inc. 2019, Retrieved from Internet on Jan. 11, 2019, 4 pgs.
Website: https://www.polar.com/us-en/club "POLAR/ Wearable heart rate tracking app with fact-based results", Copyright—Polar Electro 2019, Retrieved from Internet on Jan. 10, 2019, 11 pgs.
Website: https://www.orangetheoryfitness.com/apps/blog/post/620 "What your heart rate is telling you", Orangetheory Fitness, dated Aug. 27, 2018, Retrieved from Internet on Jan. 10, 2019, 7 pgs.

* cited by examiner

Enabled Devices:

Available Devices:

BIOLOGICAL DATA TRACKING SYSTEM AND METHOD

TECHNICAL FIELD

This disclosure relates to the field of monitoring systems utilizing data from sensors applied to living beings. More particularly, the disclosure pertains to a system for configuring and collecting data directly from a set of wearable sensors using an application that is downloadable and executable via a web browser.

BACKGROUND

A number of physiological data sensors have been developed to assist athletes during training or competition. Some of these sensors are wearable or fixed to the athlete's skin to measure various metrics and wirelessly send the measurements to a cell phone or tablet for display. Typically, each sensor is associated with an application program which a user must download and install on the cell phone or tablet. Each application receives and displays data from a single sensor. Some of the application programs may be capable of uploading data to a server for later processing.

If there are multiple athletes or one athlete using multiple sensors, multiple devices (cell phones or tablets) and/or multiple applications may be required to display the data. Any computation that relies on data from multiple sensors must rely on the data being uploaded to a server. Even then, it may be difficult to correlate the data from one sensor with the data from another sensor.

SUMMARY OF THE DISCLOSURE

A biological data tracking system includes at least one biological data sensor, a computer, and an application program. The at least one sensor may include at least two different types of sensors which may communicate with the application using different communication interfaces. The computer includes an internet connection and browser software. The application, which executes within the browser, is programmed to establish wireless communications with each of the sensors, receive streams of data from the sensors, and display, via the browser software, readings derived from streamed data. The application may also transmit commands to the sensors to change sensor settings. At least one of the readings may be derived from data streams from two different sensors. The system may also include a server configured to receive the streams of data via an internet connection and compute the readings. The server may also transmit the application program to the browser in response to a user accessing a web page.

A biological data tracking system includes an application and a server. The application establishes wireless communications with each of a plurality of wearable data sensors, receives streams of data from the sensors, and displays, via browser software, readings derived from streamed data. The server may transmit the application to the browser in response to a user accessing a web page. The application may transmit the streams of data to the server which then calculates the readings. The plurality of wearable sensors may include at least two different types of sensors, including sensors that communicate with the application using different communication interfaces. At least one of the readings may be derived based on data streams from two different sensors. The application may also transmit commands to a subset of the plurality of sensors to change sensor settings.

A method of tracking biological data includes transmitting an application from a server to a browser, detecting at least one wearable sensor, wirelessly receiving a data stream from the sensor, and displaying a reading. The server transmits the application to the browser in response to a user accessing a web page. The application detects the sensors and directly receives the data streams. The readings are derived from at least one of the data streams and displayed in the browser. The method may also include transmitting the data streams from the browser to the server and transmitting the reading from the server to the browser. The application may send a command to the sensor to change a sensor setting. The sensors may include at least two types of sensors which may transmit data streams to the application using two different communication interfaces.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
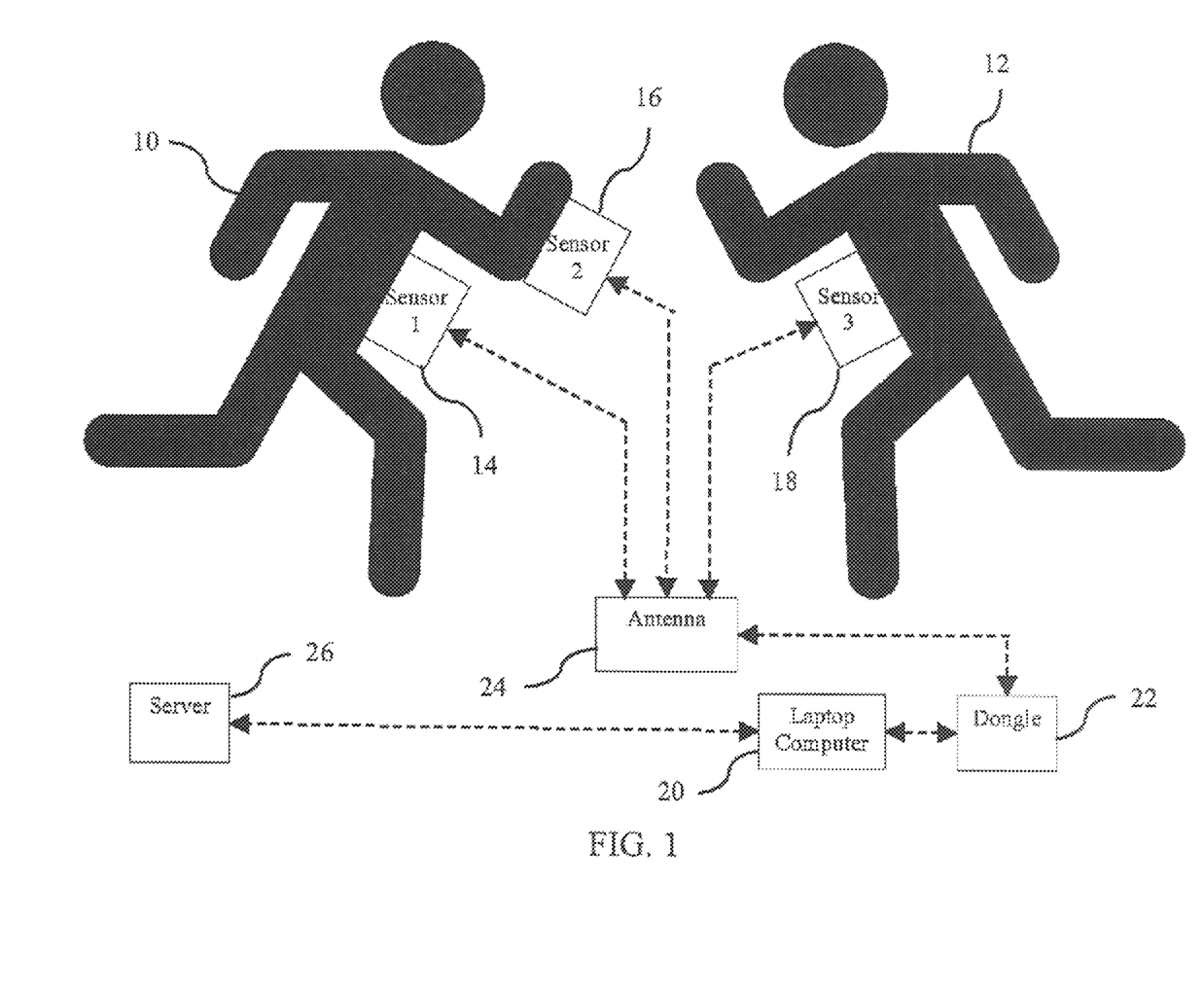
FIG. 1 is a schematic diagram of a biological data tracking system.

FIG. 1 illustrates a system to simultaneously track and analyze biological data from multiple subjects. The subjects may be, for example, athletes during training or competition. Alternatively, the subjects could be, for example, pets, livestock, or humans other than athletes. Two such subjects, 10 and 12, are shown in FIG. 1. The actual number of subjects may vary from one to several dozen or even more. Each subject is monitored by at least one wireless wearable sensor 14, 16, and 18. Wearable sensors include sensors that are attached directly to the subject's skin, sensors that are embedded under the subject's skin, and sensors that are attached to the subject's clothing. Various types of sensors detect various types of data. Some biological sensors may measure physiological metrics such as, for example, electro-cardiogram signals, blood flow, body temperature, perspiration levels, or breathing rate. Some biological sensors may detect biomechanical metrics such as, for example, position or accelerations in various directions from which a subject's movements may be characterized. In addition to biological data about the individual subject, some sensors may measure environmental conditions such as ambient temperature and humidity.

Due to the mobility of the subjects, wired connections to the sensors are often not feasible. Therefore, the sensors communicate with the other parts of the system wirelessly, for example using Bluetooth Low Energy (BLE) technology. In the embodiment of FIG. 1, the sensors communicate with a personal computer 20 via a Bluetooth dongle 22 and an antenna 24. The antenna 24 may be a directional antenna positioned to provide high gain with respect to the area in which the subjects move and low gain with respect to other areas. A carefully selected and positioned directional antenna provides multiple advantages over a non-directional antenna. First, the higher gain in the areas occupied by the subjects increases the transmission range. Secondly, especially in spectator sports, there may be a high number of signals in the same frequency range from surrounding areas that could cause interference. Many spectators have mobile phones that communicate with other devices via Bluetooth and Wifi, which uses the same frequency. An antenna with low gain toward these areas dramatically reduces the likelihood of interference. Finally, personal computer 20 is connected to a server 26 by some combination of Wifi and hardwired internet connections.

Figure 2:
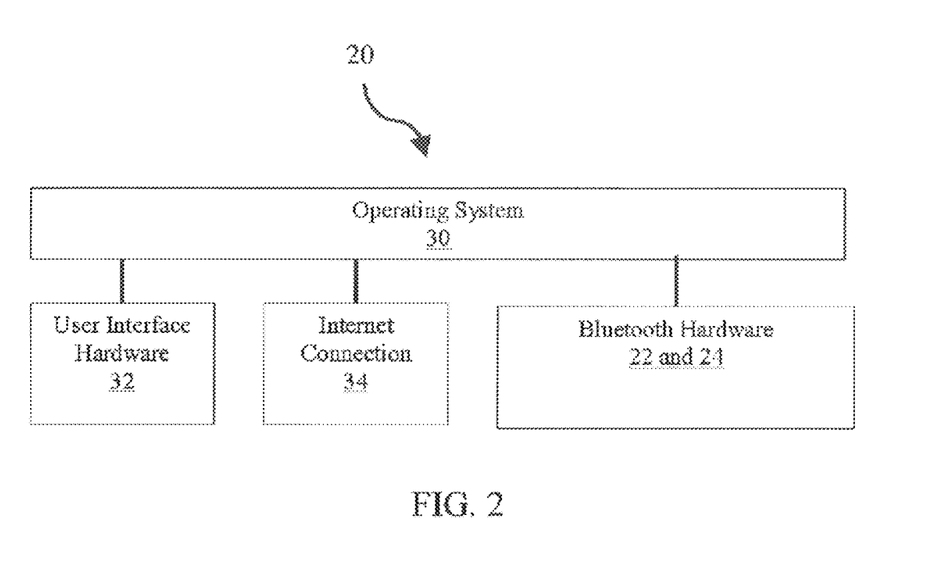
FIG. 2 is a block diagram illustrating the state of a computer system before a user launches the data tracking system webpage.

FIG. 2 illustrates the status of the system at the beginning of a data monitoring session. Personal computer 20 includes an operating system 30 that coordinates interactions between various types of hardware and software. Personal computer 20 may be, for example, a laptop computer or a desktop computer. The hardware present includes Bluetooth hardware such as the dongle 22 and antenna 24 illustrated in FIG. 1. It also includes various user interface hardware 32 such as a keyboard, a pointing device such as a mouse, and a video display. The personal computer also has an internet connection 34 which may include both hardware and software aspects.

Figure 3:
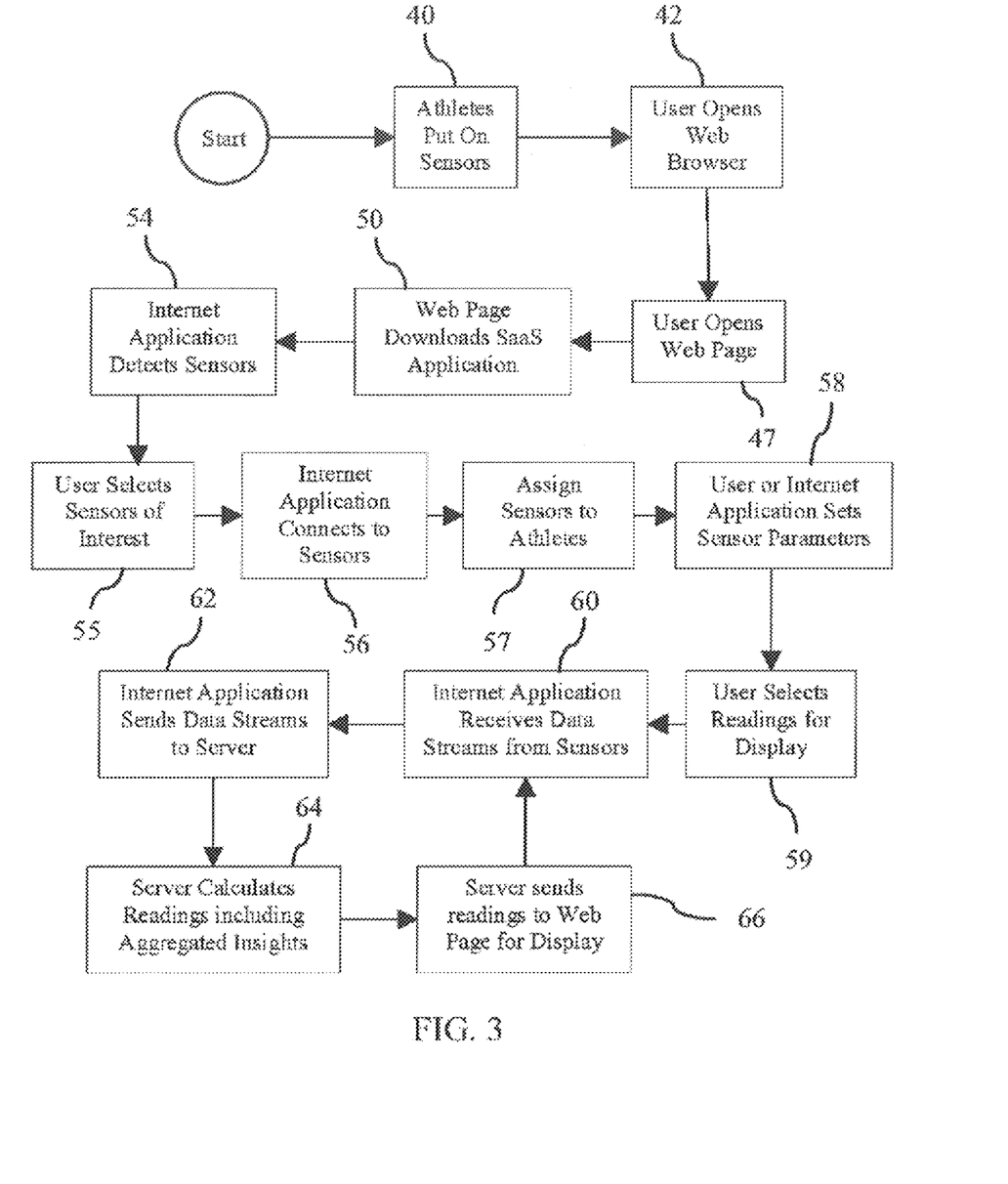
FIG. 3 is a flowchart for using the biological data tracking system of FIG. 1.
Figure 4:
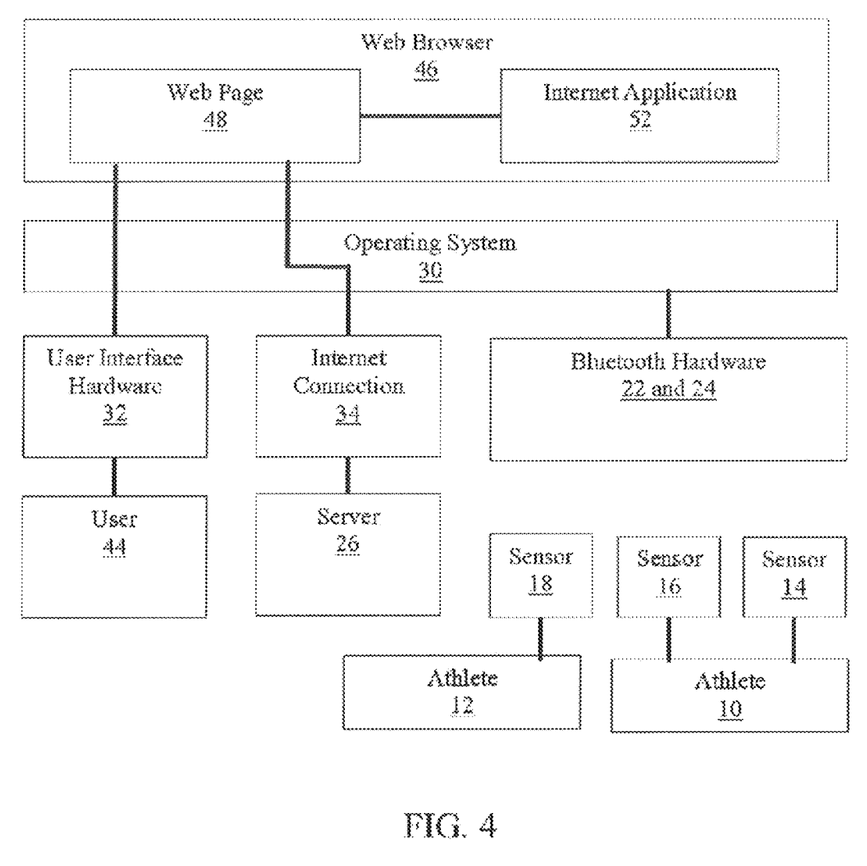
FIG. 4 is a block diagram illustrating the state of the system after an intermediate step in the method of FIG. 3.

FIG. 3 is a flow chart for a typical operational sequence of utilizing the system of FIG. 1. At 40, the subjects put on the sensors and switch them on if necessary. FIG. 4 illustrates the status of the system following step 40. Note that no connection yet exists between the sensors and the personal computer.

At 42 of FIG. 3, a user 44 (FIG. 4), interacting with the user interface hardware 32, opens a web browser 46. A web browser is a general-purpose software application that is commonly found on personal computers. A user may start the web browser by, for example, clicking on an icon with a pointing device such as a mouse. The web browser starts by displaying a default page such as a search engine. At 47, the user opens web page 48 which is associated with the tracking system of FIG. 1. The user may open this page by typing in a Uniform Resource Locator (URL), by using a search engine, or by selecting a saved entry from a previous session.

At 50, the web page 48 triggers downloading of web application 52 (FIG. 4) to the web browser. FIG. 4 illustrates the state of the system following step 50. A web page is a software entity that conveys information, usually from a server, to the user and collects information and commands from the user to be conveyed to the server. An application, on the other hand, performs non-trivial computation and may be programmed to interact with hardware besides the user interface hardware 32 and the internet connection 34. Internet Application 52 is a Software as a Service (SaaS) application, meaning that, from the user's perspective, the functionality is being provided as a service on the internet. The user does not direct, and doesn't need to be aware of, any downloading or installation of software to his or her computer.

Figure 5:
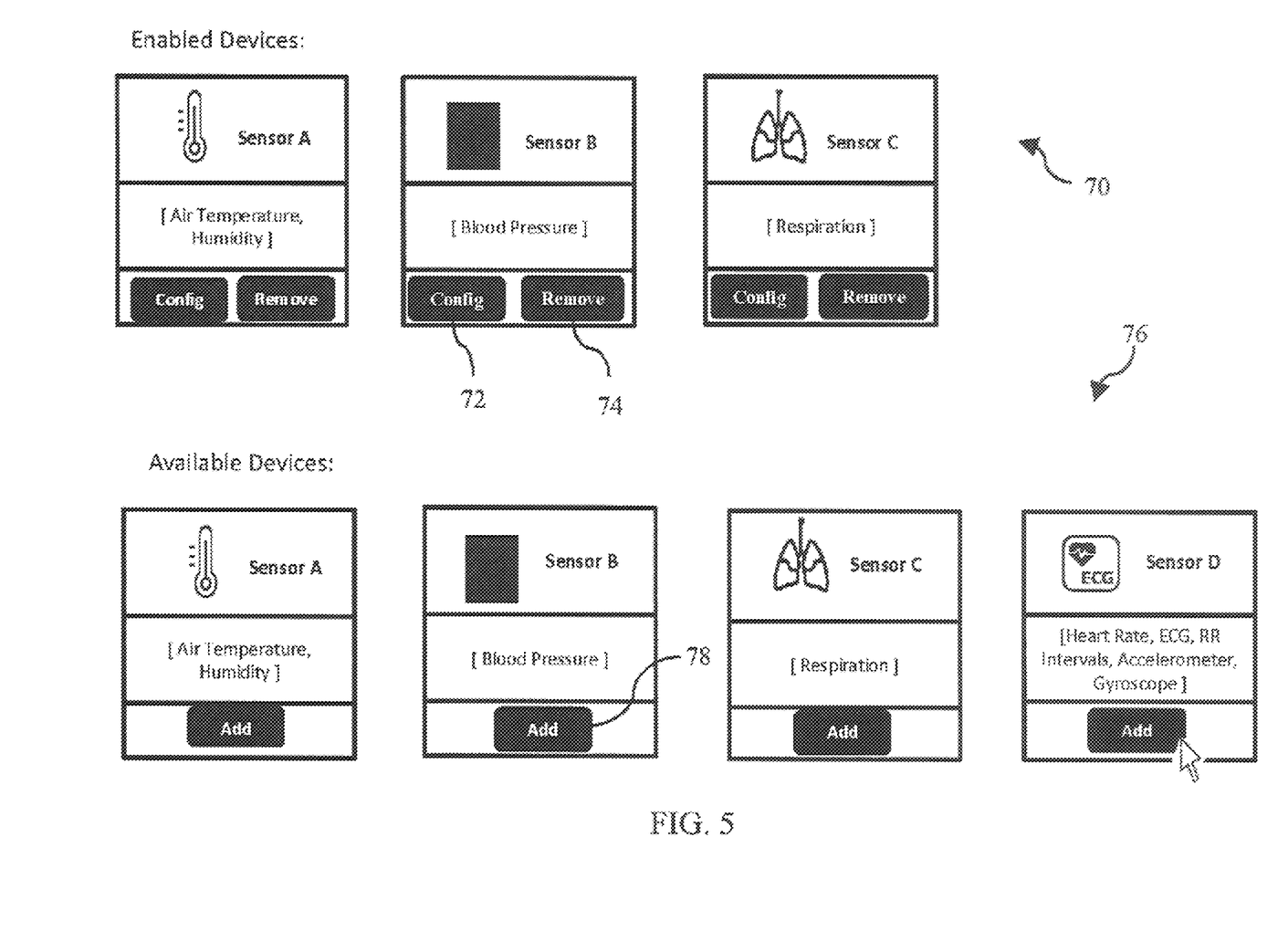
FIG. 5 is an exemplary display page for selecting sensors.

In FIG. 3, at 54, the Application 52 utilizes the Bluetooth hardware 22 and 24 to detect the presence of sensors 14, 16, and 18 and instructs web page 48 to display a list of available sensors to the user. At 55, the user selects the sensors of interest, for example, by clicking on buttons displayed by web page 48. FIG. 5 illustrates an exemplary webpage 48 for selecting sensors and setting sensor parameters. Sensors that have already been selected are displayed in a first area of the screen 70. For each such sensor, the display indicates the type of sensor, the quantities which the sensor is capable of measuring, and two buttons. Button 72 permits the user to configure the sensor as discussed below. Button 74 permits the user to un-select the sensor. Sensors that have been detected but not yet selected are displayed in a second area of the screen 76. For each such sensor, the display indicates the type of sensor, the quantities which the sensor is capable of measuring, and one button. Button 78 permits the user to select the sensor, after which it is moved to area 70.

Figure 6:
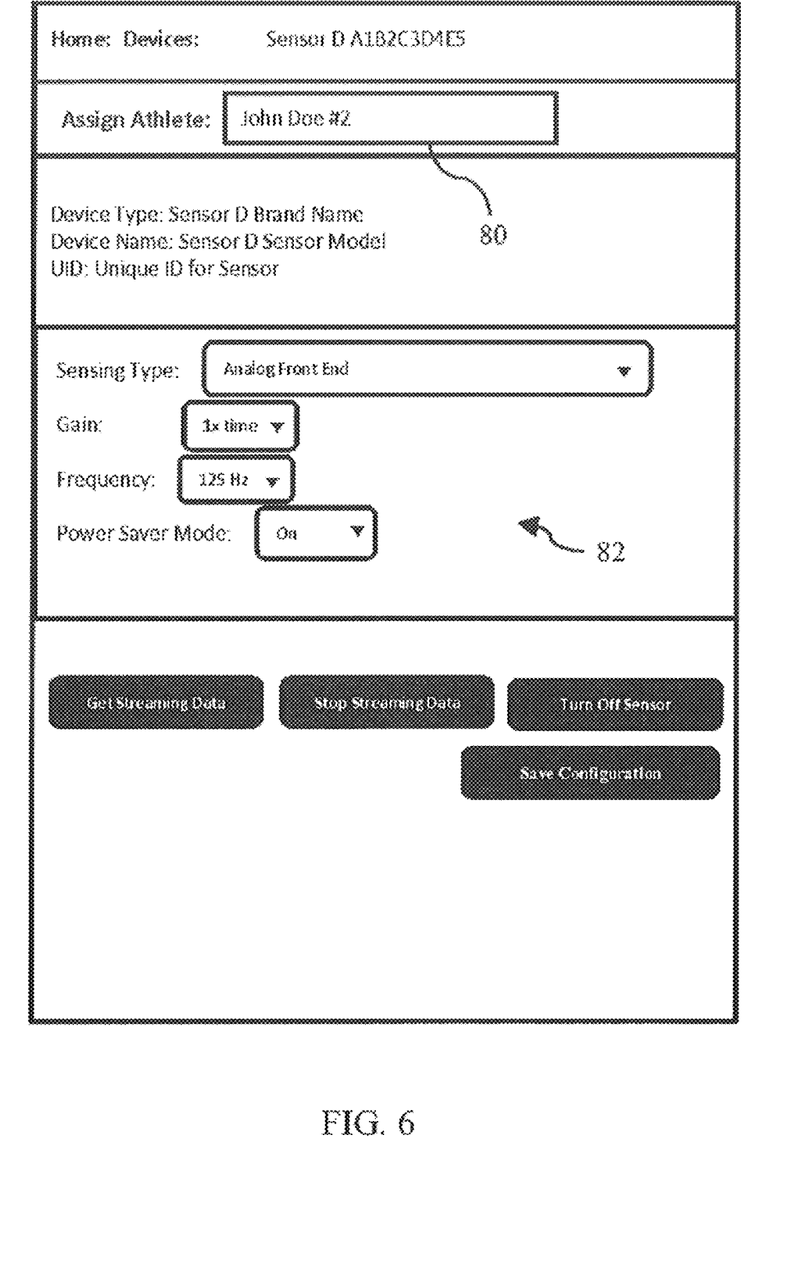
FIG. 6 is an exemplary data entry screen for assigning sensors to subjects and for setting sensor parameters.
Figure 7:
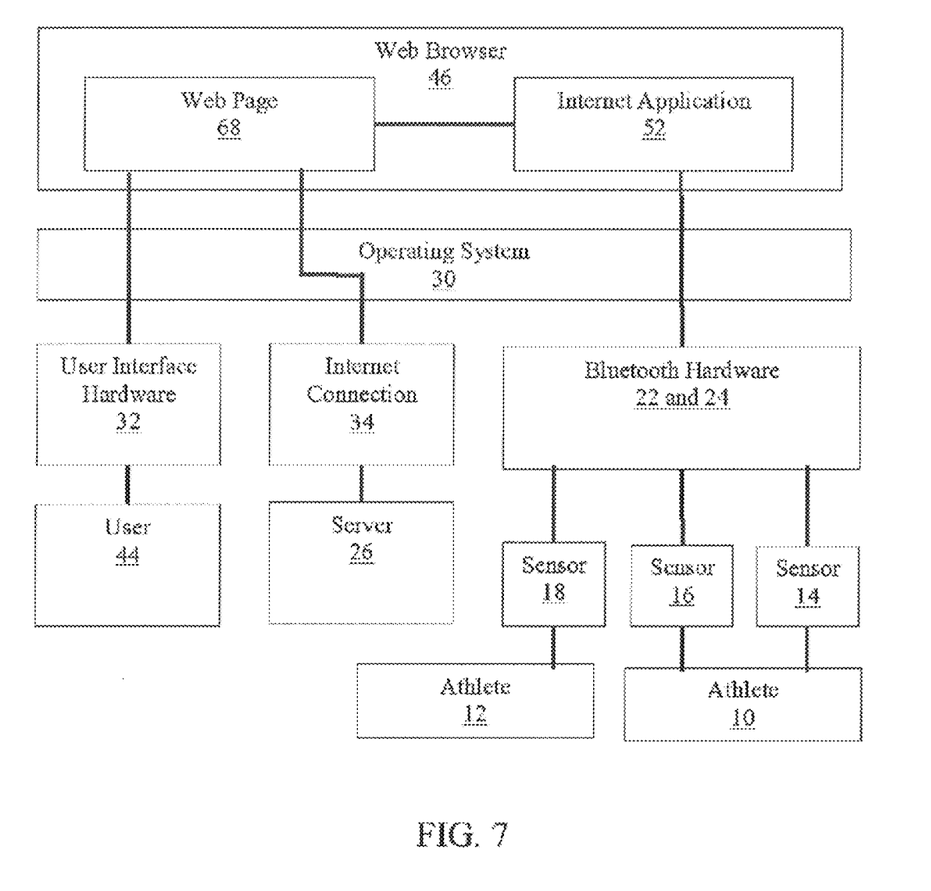
FIG. 7 is a block diagram illustrating the state of the system during an operation phase.

In FIG. 3, at 56, the application connects to the selected sensors. At 57, the user assigns particular sensors to particular subjects. The system may provide a default value to simplify this process when only one subject is involved. At 58, the application sends commands to the sensors to set sensor parameters and start streaming measurements. The parameters may include items like mode of operation, sampling rate, data range, gain, etc. The user may be presented with the ability to edit parameter settings through a data entry screen such as that illustrated in FIG. 6. Text entry box 80 permits the user to assign the sensor to a particular subject. Selection boxes in area 82 allow the user to set sensor parameters. The state of the system after selecting sensors and assigning them to subjects is illustrated in FIG. 7.

Figure 8:
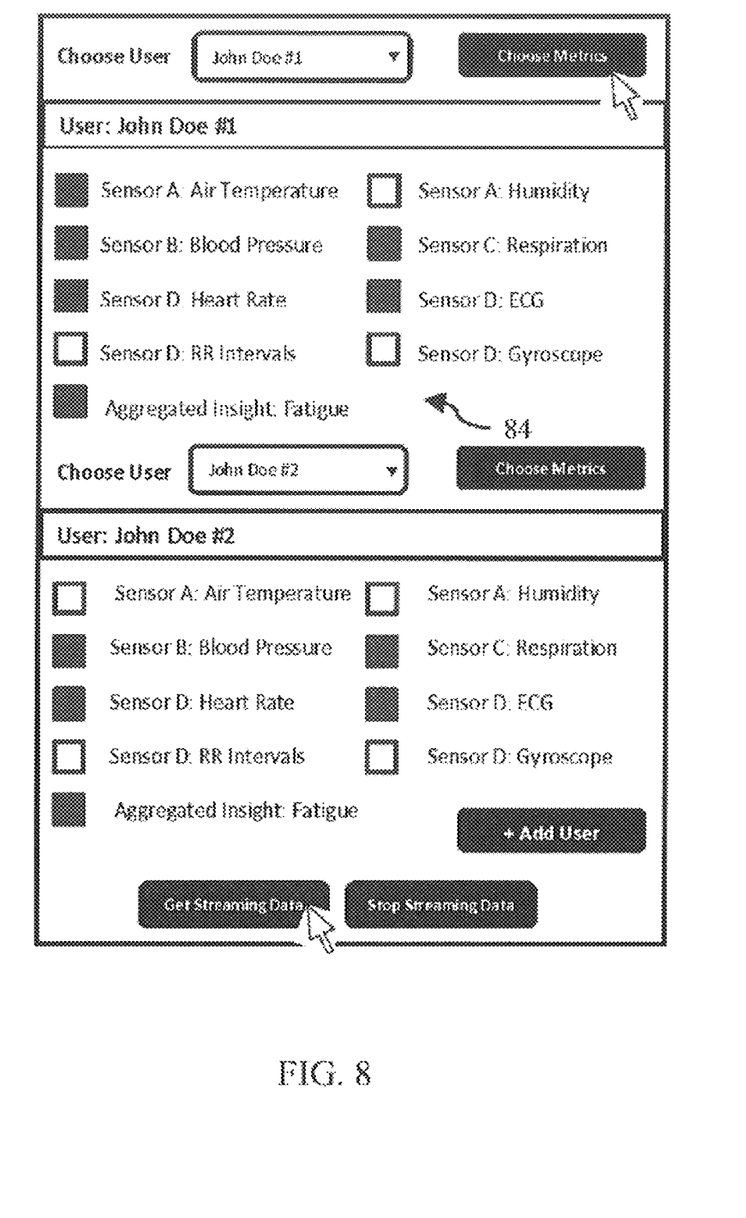
FIG. 8 is an exemplary data entry screen for selecting readings for display.

In FIG. 3, at 59, the user selects which readings should be displayed for each subject. This may be performed via a data entry screen such as that illustrated in FIG. 8. A checkbox is displayed for each measurement that is available. Note that the number of measurements available may exceed the number of selected sensors, as some sensors are capable of measuring multiple quantities. Also, some readings may be derived from multiple data streams. Such readings are called aggregated insights. Some aggregated insights may be derived from data streams from different types of sensors. For example, the fatigue reading 84 may be derived from a combination of heart rate (from an electro-cardiogram sensor), blood pressure, ambient temperature, etc. As another example, a first athlete's reaction time may be derived by comparing an acceleration measurement from the first athlete to an acceleration measurement from a second athlete. The ability to gather these different data streams in a single application greatly facilitates computation of these aggregated insights. If the data streams are collected by separate applications and then transmitted to the server, the latency of transmission may preclude real-time or near real-time display. Near real-time means low enough latency for the subject to react to the reading during the activity. Additionally, variability of latency between sensors may lead to the data streams not being properly synchronized as they arrive at the server.

Figure 9:
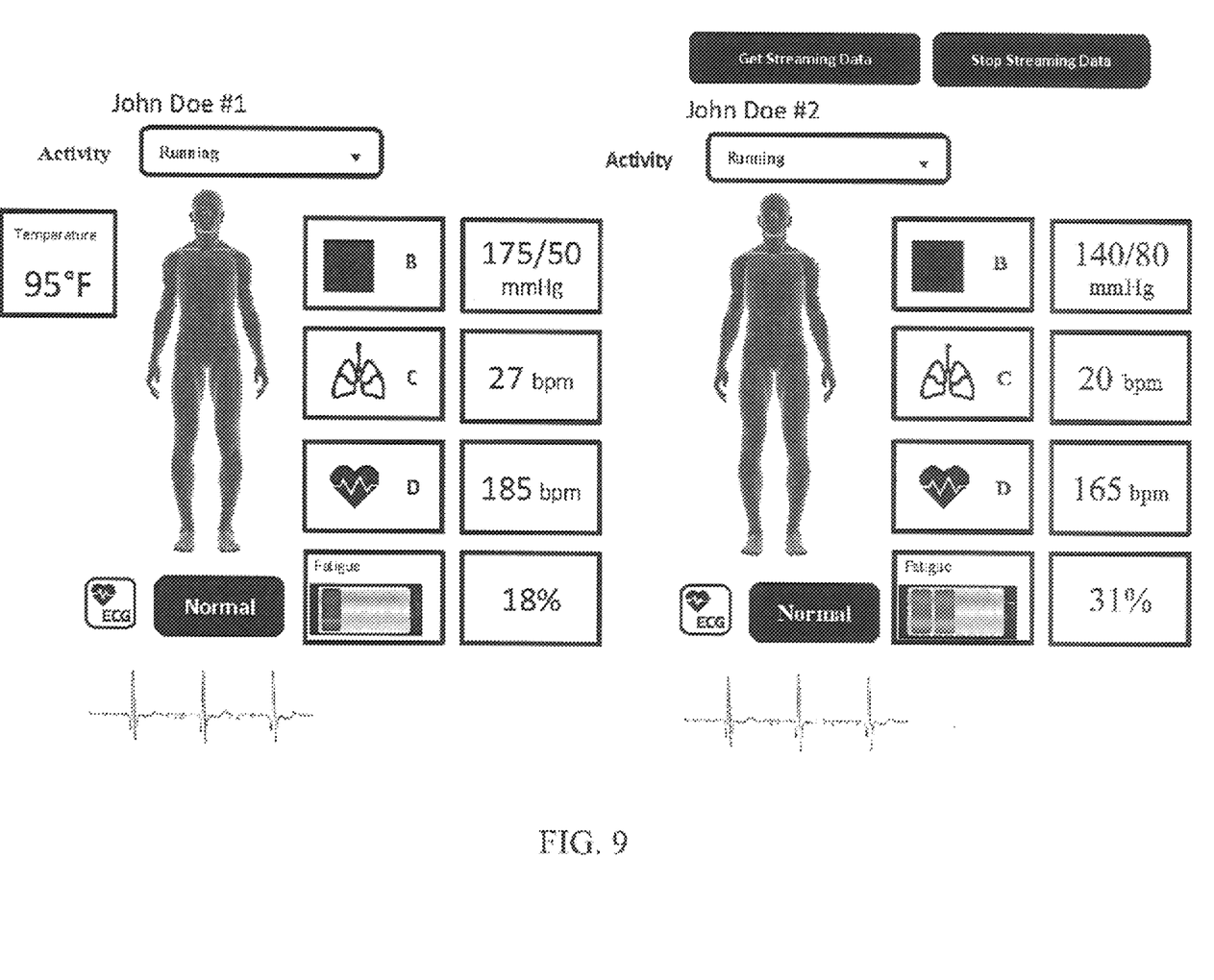
FIG. 9 is an exemplary display page for readings.

Then, the system operates in a continuous fashion with the application receiving data streams from the sensors at 60, the application sending those data streams to the server at 62, the server processing the data streams to calculate readings of interest at 64, and the server sending the readings to a web page for display at 66. For example, a data stream may involve electro-cardiogram measurements every millisecond and the server may process this stream to calculate a heart rate reading every second. FIG. 9 illustrates an exemplary webpage for displaying readings.

Different types of sensors, especially if they are provided by different manufacturers, may employ different communication interfaces. Communication interfaces include command sets, data formats, and message exchange sequences. For example, one type of sensor might begin sending measurements once every 20 milliseconds in response to a single command to begin streaming data. Another type of sensor might require that the measurement frequency be specified in the "begin streaming" command. Yet another type of sensor might send individual measurements in response to request commands such that the system must send requests commands at the desired frequency.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. As such, embodiments described as less desirable than other embodiments or prior art implementations with respect to one or more characteristics are not outside the scope of the disclosure and can be desirable for particular applications.

What is claimed is:

1. A biological data tracking system comprising:
   at least one biological data sensor;
   a computer including an internet connection and browser software; and
   a browser-based web application executing within the browser software, automatically downloaded from a server in response to a user accessing a webpage and programmed to:
   establish direct wireless communications with each biological data sensor, by detecting and connecting with each biological data sensor via the browser software;
   receive, by the direct wireless communications via the browser software, streaming data from the at least one biological data sensor as received streamed data;
   transmit, via the browser software, the received streamed data from the browser-based web application to the server which processes the received streamed data and computes readings that are transmitted back to the browser-based web application; and
   display, via the browser software, readings derived from the received streamed data wherein the browser-based web application is further programmed to transmit commands to the at least one biological data sensor to set sensor parameters, the browser-based web application being operable:
   for the user to select and assign a subset of one or more sensors from available sensors for one or more users;
   for the user to select a subset of one or more metrics from available metrics from which the which corresponding readings for one or more users are displayed;
   for the user to initiate a single command that provides instructions concurrently to each selected sensor amongst a plurality of selected sensors to send streamed data from each of the selected sensors, wherein the browser-based web application receives the streamed data from each of the selected sensors and wherein the streamed data consists of multiple data metrics; and
   to track multiple users simultaneously, wherein a single browser-based web application is operable to gather different data streams from different types of sensors for each user simultaneously.

2. The biological data tracking system of claim 1 further comprising a server configured to receive the streamed data via the internet connection and compute the readings.

3. The biological data tracking system of claim 2 wherein the server is further configured to transmit the browser-based web application to the browser software in response to the user accessing a web page.

4. The biological data tracking system of claim 1 wherein the at least one biological data sensor includes at least two different types of sensors.

5. The biological data tracking system of claim 4 wherein the at least two different types of sensors communicate with the browser-based web application using different communication—interfaces, the different communication-interfaces including at least one of: command sets, data formats, or message exchange sequences.

6. The biological data tracking system of claim 4 wherein at least one reading of the readings is derived from data streams from-the at least two different types of sensors.

7. A biological data tracking system comprising:
   a server; and
   a browser-based web application, executable within a web browser and automatically downloaded from the server to the web browser and in response to a user accessing a webpage, programmed to establish direct wireless communications with a plurality of wearable sensors by detecting and connecting with each wearable sensor via the browser-based web application, receive streams of data from the plurality of wearable sensors by the direct wireless communications via the web browser as streamed data, and display readings derived from the streamed data,
   wherein the server is configured to transmit the browser-based web application to the web browser in response to the user accessing a web page and wherein the browser-based web application is further programmed to transmit commands to at least one wearable sensor to set sensor parameters, the browser-based web application also being operable:
   for the user to select and assign a subset of one or more sensors from available sensors for one or more users;
   for the user to select a subset of one or more metrics from available metrics from which the which corresponding readings for one or more users are displayed;

for the user to initiate a single command that provides instructions concurrently to each selected sensor amongst a plurality of selected sensors to send the streamed data from each of the selected sensors, wherein the browser-based web application receives the streamed data from each of the selected sensors and wherein the streamed data consists of multiple data metrics; and to track multiple users simultaneously, wherein a single browser-based web application is operable to gather different data streams from different types of sensors for each user simultaneously.

8. The biological data tracking system of claim 7 wherein:
the browser-based web application transmits the streamed data to the server; and
the server calculates the display readings.

9. The biological data tracking system of claim 7 wherein the plurality of wearable sensors includes at least two different types of sensors.

10. The biological data tracking system of claim 9 wherein the at least two different types of sensors amongst the plurality of wearable sensors communicate with the browser-based web application using different communication interfaces.

11. The biological data tracking system of claim 7 wherein at least one reading of the display readings is derived based on data streams from two different sensors.

12. The biological data tracking system of claim 7 wherein the browser-based web application is further programmed to transmit commands to a subset of the plurality of wearable sensors to change sensor parameters.

13. A method of tracking biological data comprising:
transmitting a browser-based web application from a server to a browser that is automatically downloaded to the browser in response to a user accessing a-web page;
detecting, via the browser-based web application, at least one wearable sensor;
connecting, via the browser-based web application, directly to the at least one wearable sensor;
wirelessly receiving, via the browser-based web application, data streams from each wearable sensor;
displaying, within the browser, a reading derived from at least one of the data streams; and
transmitting commands to the at least one wearable sensor to set sensor parameters, the browser-based web application being operable:
for the user to select and assign a subset of one or more sensors from available sensors for one or more users;
for the user to select a subset of one or more metrics from available metrics from which corresponding readings for one or more users are displayed;
for the user to initiate a single command that provides instructions concurrently to each selected sensor amongst a plurality of selected sensors to send the streamed data from each of the selected sensors, wherein the browser-based web application receives the streamed data from each of the selected sensors and wherein the streamed data consists of multiple data metrics; and to track multiple users simultaneously, wherein a single browser-based web application is operable to gather different data streams from different types of sensors for each user simultaneously.

14. The method of claim 13 further comprising:
transmitting the data streams from the browser to the server; and
transmitting the reading from the server to the browser.

15. The method of claim 13 further comprising sending a command from the browser-based web application to the at least one wearable sensor to change a sensor setting.

16. The method of claim 13 wherein the at least one wearable sensor includes at least two different types of sensors.

17. The method of claim 16 wherein at least two types of sensors transmit data streams to the browser-based web application using two different communication—interfaces, the two different communication interfaces including at least one of: command sets, data formats, or message exchange sequences.

18. The method of claim 16 wherein the reading is derived from data streams from more than one sensor.

19. The biological data tracking system of claim 1 wherein the browser-based web application is operable to monitor multiple users.

20. The biological data tracking system of claim 1 wherein the sensor parameters include a at least one of: mode of operation, sampling rate, data range, gain, sensing type, power off mode, or power save mode.

21. The biological data tracking system of claim 1 wherein the browser-based web application is operable to save the sensor parameters for one or more sensors based upon-user input.

22. The biological data tracking system of claim 1 wherein the user can select one or more sensors to receive streamed data.

23. The biological data tracking system of claim 1 wherein the browser-based web application is operable to derive one or more real-time or near real-time aggregated insights from data streams from different types of sensors for each user based upon the data streams being collected by the single browser-based web application, wherein near real-time means low enough latency for the user to react to readings during activity.

24. The biological data tracking system of claim 1 wherein the browser-based web application is a Software-as-a-Service application.

25. The biological data tracking system of claim 1 wherein the streamed data includes a portion of non-biological data.

* * * * *

UNITED STATES PATENT AND TRADEMARK OFFICE
CERTIFICATE OF CORRECTION

PATENT NO. : 11,382,510 B2
APPLICATION NO. : 16/274701
DATED : July 12, 2022
INVENTOR(S) : Vivek Khare et al.

It is certified that error appears in the above-identified patent and that said Letters Patent is hereby corrected as shown below:

In the Claims

Column 6, Lines 65-66, Claim 7:
After "one or more metrics from available metrics from which"
Delete "the which"

Signed and Sealed this
Ninth Day of May, 2023

*Katherine Kelly Vidal*
Katherine Kelly Vidal
*Director of the United States Patent and Trademark Office*